US009759709B1

(12) United States Patent
Kaushik et al.

(10) Patent No.: US 9,759,709 B1
(45) Date of Patent: Sep. 12, 2017

(54) DEVICES AND METHODS TO MONITOR HIV-INFECTION IN PRESENCE OF SUBSTANCE OF ABUSE AND/OR THERAPEUTIC AGENT

(71) Applicants: Ajeet Kaushik, Doral, FL (US); Madhavan Nair, Coral Gables, FL (US)

(72) Inventors: Ajeet Kaushik, Doral, FL (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/267,605

(22) Filed: Sep. 16, 2016

(51) Int. Cl.
| | |
|---|---|
| C12N 5/00 | (2006.01) |
| G01N 33/483 | (2006.01) |
| G01N 33/50 | (2006.01) |
| G01N 33/94 | (2006.01) |
| G01N 27/327 | (2006.01) |
| G01N 27/414 | (2006.01) |
| G01N 27/02 | (2006.01) |

(52) U.S. Cl.
CPC ....... *G01N 33/4836* (2013.01); *G01N 27/026* (2013.01); *G01N 27/327* (2013.01); *G01N 27/4145* (2013.01); *G01N 33/5058* (2013.01); *G01N 33/946* (2013.01); *G01N 2333/16* (2013.01); *G01N 2800/26* (2013.01)

(58) Field of Classification Search
CPC ............. G01N 33/4836; G01N 27/026; G01N 33/5058; G01N 33/946; G01N 2333/16; G01N 2800/26
See application file for complete search history.

(56) References Cited

PUBLICATIONS

Cui et al., Microelectrode array biochip: tool for in vitro drug screening based on the detection of a drug effect on dopamine release from PC12 cells. Analytical Chemistry, vol. 78, No. 18 (2006) pp. 6347-6355.*
Heiskanen et al., "Chip Based Electroanalytical Systems for Monitoring Cellular Dynamics." in: Kakaç S., Kosoy B., Li D., Pramuanjaroenkij A. (eds.) Microfluidics Based Microsystems, NATO Science for Peace and Security Series A: Chemistry and Biology. (Springer, Dordrecht, 2010), pp. 399-426.*
Atluri, V.S.R., et al., "Human Synaptic Plasticity Gene Expression Profile and Dendritic Spine Density Changes in HIV-Infected Human CNS Cells: Role in HIV-Associated Neurocognitive Disorders (HAND)." PLoS One, Apr. 2013, 8(4): 1-11, e61399.
Barré-Sinoussi, F., et al., "Past, present and future: 30 years of HIV research." Nature Reviews Microbiology, Dec. 2013, 11(12): 877-Abstract.
Cheng, Xuanhong, et al., "Cell detection and counting through cell lysate impedance spectroscopy in microfluidic devices." Lab on a Chip, 2007, 7(6): 746-755.
Cohen, A.E.; Kunz, R.R., "Large-area interdigitated array microelectrodes for electrochemical sensing." Sensors and Actuators B, 2000, 62: 23-29.
Cruz, A.F.D., et al., "A low-cost miniaturized potentiostat for point-of-care diagnosis." Biosensors and Bioelectronics, 2014, 62: 249-254.
Dahal, S., et al., "Interactive effects of cocaine on HIV infection: implication in HIV-associated neurocognitive disorder and neuroAIDS." Frontiers in Microbiology, Sep. 2015, 6(931): 1-7.
Eugenin, E.A.; Berman, J.W., "Gap Junctions Mediate Human Immunodeficiency Virus-Bystander Killing in Astrocytes." The Journal of Neuroscience, Nov. 2007, 27(47): 12844-12850.
Iwasaki, Y.; Morita, M., "Electrochemical Measurements with Interdigitated Array Microelectrodes." Current Separations, 1995, 14(1): 2-8.
Jayant, R.D., et al., "Sustained-release nanoart formulation for the treatment of neuroAIDS." International Journal of Nanomedicine, Feb. 2015, 10: 1077-1093.
Karim, W.A., et al., "Effectiveness and Safety of Tenofovir Gel, an Antiretroviral Microbicide, for the Prevention of HIV Infection in Women." Science, Sep. 2010, 329(5996): 1168-1174.
Katz, J.L., et al., "Behavioral effects of rimcazole analogues alone and in combination with cocaine." European Journal of Pharmacology, 2003, 468(2): 109-119.
Kaushik, A., et al., "Electrochemical monitoring-on-chip (E-MoC) of HIV-infection in presence of cocaine and therapeutics." Biosensors and Bioelectronics, 2016, 86: 426-431.
Kaushik, A., et al., "Electrochemical sensing method for point-of-care cortisol detection in human immunodeficiency virus-infected patients." International Journal of Nanomedicine, Jan. 2015, 10(10): 677-685.

(Continued)

*Primary Examiner* — Kara Johnson
(74) *Attorney, Agent, or Firm* — Saliwanchik, Lloyd & Eisenschenk

(57) ABSTRACT

The subject invention provides materials and methods for detecting the presence and progression of human immunodeficiency virus (HIV) infections in the presence of a substance of abuse and/or at least one therapeutic agent. Preferred embodiments provide that the detection of HIV infection is accomplished by applying electrochemical impedance spectroscopy to an apparatus comprising cultured cells of the central nervous system (CNS) such as, for example, human astrocytes (HA), and/or of the peripheral nervous system (PNS) in contact with at least one sensing electrode. In some embodiments, the detection apparatus can be integrated with electronic components such as, for example, microelectromechanical systems (MEMS), nanoelectromechanical systems (NEMS), and miniaturized potentiostats. Advantageously, technology provided herein enables rapid (e.g., less than 20 minute) assessment of HIV infections suitable for point-of-care (POC) disease monitoring and treatment.

6 Claims, 5 Drawing Sheets

(56) References Cited

PUBLICATIONS

Kaushik, A., et al., "Magnetically guided central nervous system delivery and toxicity evaluation of magneto-electric nanocarriers." *Scientific Reports*, May 2016, 6(25309): 1-10.

Kaushik, A., et al., "Nano-biosensors to detect beta-amyloid for Alzheimer's disease management." *Biosensors and Bioelectronics*, 2016, 80: 273-287.

Kaushik, A., et al., "Nanostructured Iron Oxide Platform for Impedimetric Cholesterol Detection." *Electroanalysis*, 2010, 22(10): 1045-1055.

Kaushik, A., et al., "The potential of magneto-electric nanocarries for drug delivery." *Expert Opinion on Drug Delivery*, Oct. 2014, 11(10): 1635-1646.

Kaushik, A., et al., "Recent advances in cortisol sensing technologies for point-of-care application." *Biosensors and Bioelectronics*, 2014, 53: 499-512.

Kaushik, A., et al., "Towards detection and diagnosis of Ebola virus disease at point-of-care." *Biosensors and Bioelectronics*, 2016, 75: 254-272.

Kurapati, K.R.V., et al., "Combinatorial cytotoxic effects of *Curcuma longa* and *Zingiber officinale* on the PC-3M prostate cancer cell line." *J Basic Clin Physiol Pharmacol*, 2012, 23(4): 139-146.

Luongo, K., et al., "Microfluidic device for trapping and monitoring three dimensional multicell spheroids using electrical impedance spectroscopy." *Biomicrofluidics*, 2013, 7(3): 034108.

Mahmoud, K.A.; Luong, J.H., "Impedance Method for Detecting HIV-1 Protease and Screening for Its Inhibitors Using Ferrocene-Peptide Conjugate/Au Nanoparticle/Single-Walled Carbon Nanotube Modified Electrode." *Analytical Chemistry*, 2008, 80(18): 7056-7062—Abstract only.

Matsumoto, R.R., et al., "Rimcazole analogs attenuate the convulsive effects of cocaine: correlation with binding to sigma receptors rather than dopamine transporters." *Neuropharmacology*, 2001, 41(7): 878-886.

Nair, M., et al., "Getting into the brain: Potential of nanotechnology in the management of NeuroAIDS." *Advanced Drug Delivery Reviews*, 2016, 103: 202-217.

Roy, U., et al., "DJ1 expression downregulates in neuroblastoma cells (SK-N-MC) chronically exposed to HIV-1 and cocaine." *Frontiers in Microbiology*, Jul. 2015, 6(749): 1-9.

Ruiz, A., et al., "Recent update in NanoCure of NeuroAIDS." *ScienceJet*, 2015, 4(172): 1-9.

Shafiee, H., et al., "Acute HIV detection by viral lysate impedance spectroscopy on a microchip." *Solid-State Sensors, Actuators and Microsystems*, 2013, doi. 10.1109/Transducers.2013.6627225—Abstract only.

Shafiee, H., et al., "Acute On-Chip HIV Detection Through Label-Free Electrical Sensing of Viral Nano-Lysate." *Small*, 2013, 9(15): 2553-2563.

Shafiee, H., et al., "Emerging Technologies for Point-of-Care Management of HIV Infection." *Annual Review of Medicine*, 2015, 66: 387-405.

Shafiee, H., et al., "Nanostructured Optical Photonic Crystal Biosensor for HIV Viral Load Measurement." *Scientific Reports*, Feb. 2014, 4(4116): 1-7.

Shafiee, H., et al., "Paper and Flexible Substrates as Materials for Biosensing Platforms to Detect Multiple Biotargets." *Scientific Reports*, Mar. 2015, 5(8719): 1-9.

Shafiee, H., et al., "Printed Flexible Plastic Microchip for Viral Load Measurement through Quantitative Detection of Viruses in Plasma and Saliva." *Scientific Reports*, Jun. 2015, 4(9919): 1-9.

Shah, P., et al., "Chip based single cell analysis for nanotoxicity assessment." *Analyst*, Jan. 2014, 139(9): 2088-2098.

Tokel, O., et al., "Portable Microfluidic Integrated Plasmonic Platform for Pathogen Detection." *Scientific Reports*, Mar. 2015, 5(9152): 1-9.

Vasudev, A., et al., "An LTCC-based microfluidic system for label-free, electrochemical detection of cortisol." *Sensors and Actuators B: Chemical*, 2013, 182: 139-146.

Yager, P., et al., "Point-of-Care Diagnostics for Global Health." *Annu. Rev. Biomed. Eng.*, 2008, 10: 107-144.

Yang, Y., et al., "Cocaine Potentiates Astrocyte Toxicity Mediated by Human Immunodeficiency Virus (HIV-1) Protein gp120." *PLoS One*, Oct. 2010, 5(10): 1-9, e13427.

Yndart, A., et al., "Investigation of Neuropathogenesis in HIV-1 Clade B and C Infection Associated with IL-33 and ST2 Regulation." *ACS Chemical Neuroscience*, Jun. 2015, 6(9): 1600-1612.

\* cited by examiner

A = HA, B = HA + HIV,
C = HA + HIV + Tef,
D = HA + Coc,
E = HA + Coc + RA,

F = ACs + HIV + Coc,
G = ACs + HIV + Coc + Ant,
H = ACs + HIV + Coc + Tef,
I = ACs + HIV + Coc + Ant + Tef

A = HA, B = HA + HIV,
C = HA + HIV + Tef,
D = HA + Coc,
E = HA + Coc + RA,

F = HA + HIV + Coc,
G = HA + HIV + Coc + RA,
H = HA + HIV + Coc + Tef,
I = HA + HIV + Coc + Ant + Tef

DEVICES AND METHODS TO MONITOR HIV-INFECTION IN PRESENCE OF SUBSTANCE OF ABUSE AND/OR THERAPEUTIC AGENT

BACKGROUND OF INVENTION

Despite significant advancements made in the development of anti-retroviral (ARV) therapeutics, infections caused by human immunodeficiency virus (HIV-1) remain a serious threat to human health (Nair et al.; Ruiz et al. 2015). At the early stage of infection, HIV virus penetrates the blood-brain-barrier (BBB) to enter the central nervous system (CNS), causing neuroAIDS as well as the development of latent HIV reservoirs in the CNS (Jayant et al. 2015; Ruiz et al. 2015). Because the natural integrity of the BBB inhibits anti-HIV drugs to penetrate the brain, treatment of neuroAIDS still remains a challenge. Progression of HIV infection can gradually cause neuro-inflammation, neurodegeneration, and other related diseases such as, for example, HIV-encephalitis (HIVE) (Jayant et al. 2015).

Subsequent to the introduction of combination antiretroviral therapy (ART), HIV-infection-related morbidity and mortality have dramatically decreased; however, currently available antiretroviral agents, such as those involved in highly active antiretroviral therapy (HAART) exhibit certain side effects (e.g., neuro-inflammation), and can inadvertently contribute to the occurrence of neurocognitive impairments such as, for example, memory loss and sleep disturbances (Jayant et al. 2015).

Additionally, neurological disorders associated with HIV-infection can become more severe with patients who consume substances of abuse such as, for example, cocaine (Coc) (Dahal et al. 2015). Coc alters HIV patients' neurobehavior and secretion of neurotransmitters, speeds up cell-to-cell viral infection by as much as 200 times, and facilitates the virus to penetrate the BBB, resulting in the worsening of neuroAIDS disorders. Moreover, Coc is involved in inducing neuronal apoptosis via triggering viral products and potentiates astrocyte toxicity (Dahal et al. 2015). As a result, a better understanding of the progression of HIV infection at cellular level, the potential effects of Coc in HIV patients' brain functions, and the effects of drug resistance upon exposure of Coc in HIV-infected patients is of great diagnostic significance. Such understanding is required to manage and treat disorders such as neuroAIDS in a timely manner.

Considerable efforts have been made to develop novel therapeutic nanoformulations capable of treating CNS disorders caused by HIV infections (Kaushik et al. 2016a; Kaushik et al. 2014a). Currently, enzyme-linked immunosorbent immunoassay (ELISA), real time/quantitative polymerase chain reaction (RT/Q-PCR), and western blot are the most commonly used analytical tools for monitoring HIV infection by estimating p24 antigen, LTR level, and/or protein expression (Shafiee et al. 2015c; Yager et al. 2008). Optical assays-based surface plasmon resonance (SPR) system has also shown utility in quantifying CD4+ cells for detecting the progression of HIV infections (Shafiee et al. 2015c; Yager et al. 2008). Unfortunately, these methods are expensive, time consuming (e.g., a turnaround detection time is on the order of 6-8 hours), and require technical expertise in implementation.

Thus, developing a rapid, sensitive, laboratory-free, point-of-care (POC) analytical tool with reduced form factors (e.g., miniaturized, nanostructure, or paper-based) capable of detecting and monitoring the progression of HIV infections in the CNS remains a critical need.

BRIEF SUMMARY

The subject invention provides materials and methods for detecting the presence and progression of human immunodeficiency virus (HIV) infections in the presence of a substance of abuse and/or at least one therapeutic agent.

Preferred embodiments provide that the detection of HIV infection is accomplished by applying electrochemical impedance spectroscopy (EIS) to an apparatus comprising cultured cells of the central nervous system (CNS) and/or the peripheral nervous system (PNS) in contact with at least one sensing electrode. In exemplary embodiments, the cells are human astrocytes (HA).

In some embodiments, the detection apparatus can be integrated with electronic components such as, for example, microelectromechanical systems (MEMS), nanoelectromechanical systems (NEMS), and miniaturized potentiostats. Advantageously, technology provided herein enables rapid (e.g., less than 20 minute) assessment of HIV infections suitable for point-of-care (POC) disease monitoring and treatment.

BRIEF DESCRIPTION OF THE DRAWINGS

FIG. 3A compares $R_{ct}$ values between species A, B, and C, corresponding to treatment with HA, HA+HIV infection, and HA+HIV infection+Tef, respectively. FIG. 3B compares $R_{ct}$ values between species A, D, and E, corresponding to treatment with HA, HA+Coc, and HA+Coc+RA. FIG. 3C compares $R_{ct}$ values between species A, B, D, F, and I, corresponding to HA, HA+HIV-infection, HA+Coc, HA+HIV+Coc, and HA+HIV-infection+Coc+RA+Tef, respectively. FIG. 3D compares variations in $R_{ct}$ as a function of all treatment combinations A-I. The EIS measurements were performed in 400 µL of 5 mM PBS (pH 7.4) comprising 5 mM Fe (II)/Fe(III) as redox moieties.

FIG. 4A compares $R_{ct}$ values between species A, B, and C, corresponding to treatment with HA, HA+HIV, and HA+HIV+Tef, respectively. FIG. 4B compares $R_{ct}$ values between species A, D, and E, corresponding to treatment with HA, HA+Coc, and HA+Coc+RA. FIG. 4C compares $R_{ct}$ values between species A, B, D, F, and I, corresponding to HA, HA+HIV, HA+HIV+Coc, and HA+HIV+Coc+RA+Tef, respectively. FIG. 4D compares variations in $R_{ct}$ as a function of all treatment combinations A-I. The CV measurements were performed in 400 µL of 5 mM PBS (pH 7.4) comprising 5 mM Fe (II)/Fe(III) as redox moieties. The results of the CV measurements validated the results of the EIS measurements.

DETAILED DISCLOSURE

Figures 1A, 1B:
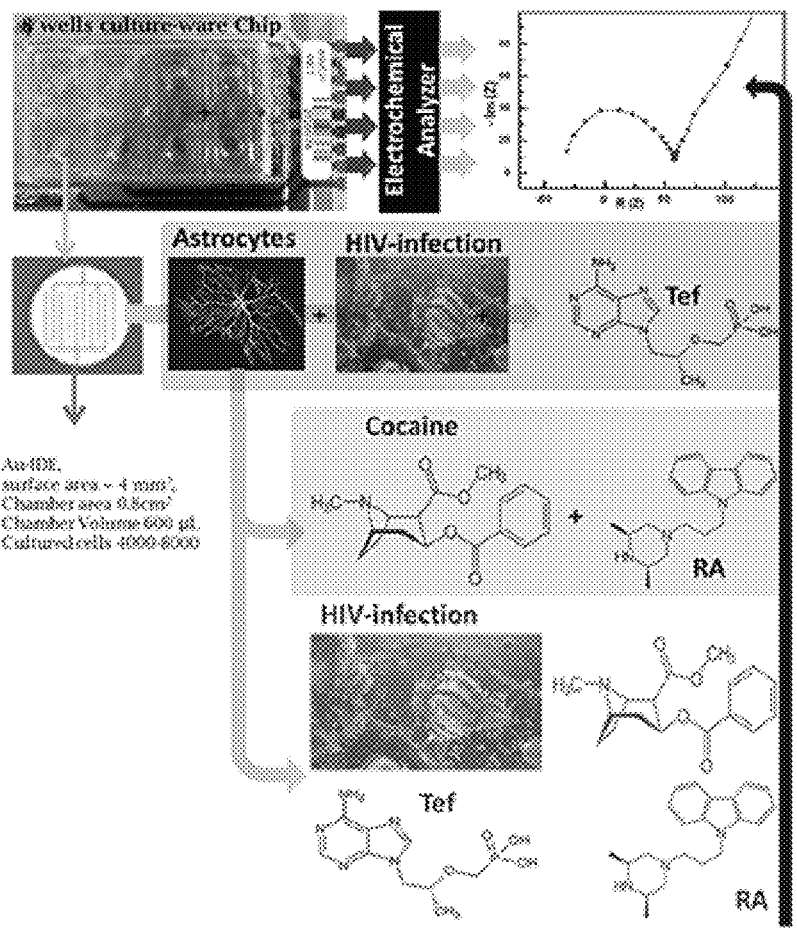
FIG. 1A illustrates the adverse effects of cocaine on HIV-infected patients.
FIG. 1B shows an exemplary protocol of using an Au-IDE based electrochemical sensing substrate integrated with a cell cultureware to monitor the progression of HIV infection in human astrocytes (HA) exposed to cocaine and other drugs such as tenofovir (Tef) and rimcazole antagonist (RA). As indicated by the blue arrow, variation in HIV infection upon cocaine exposure and subsequent treatment with specific drugs is responsive to measurements in electrochemical impedance spectroscopy (EIS).

The subject invention provides materials and methods for detecting the presence and progression of human immunodeficiency virus (HIV) infections in the presence of a substance of abuse and/or at least one therapeutic agent.

Preferred embodiments provide that the detection of HIV infection is accomplished by applying electrochemical impedance spectroscopy (EIS) to an apparatus comprising cultured cells from the central nervous system (CNS) and/or the peripheral nervous system (PNS) in contact with at least one sensing electrode. In exemplary embodiments, the cells are human astrocytes (HA).

In some embodiments, the detection apparatus can be integrated with electronic components such as, for example, microelectromechanical systems (MEMS), nanoelectromechanical systems (NEMS), and miniaturized potentiostats. Advantageously, technology provided herein enables rapid (e.g., less than 20 minute) assessment of HIV infections suitable for point-of-care (POC) disease monitoring and treatment.

In one aspect, the subject invention provides sensing devices capable of measuring the electrophysiology of cells, particularly the electrochemical impedance of cells found in the CNS and the PNS. In exemplary embodiments, the cells are human astrocytes (HA).

In some embodiments, the device provided herein comprises a working electrode, which is a sensing substrate configured with a plurality of parallel microband arrays of interdigitated electrodes (IDEs). When each electrode is potenjostated individually, one electrode is held at a potential to drive an oxidation reaction, while the adjacent electrode is held at a potential to drive a reduction reaction. Electroactive species generated at one electrode can diffuse across a small gap, with a width typically no more than 10 µm, and are subsequently converted back to their original charge. This cyclic exchange of charges between two adjacent microelectrodes fabricated in an interdigitated pattern can greatly amplify the magnitude of the current output of the overall device. As a result, sensing substrates comprising IDEs have improved detection sensitivity as a result of the increased current output generated by the microfabricated pattern. Advantageously, the sensing substrate comprising IDEs as provided herein is capable of achieving a low detection limit such as, for example, on the orders of micromolar (µM) or even picomolar (pM).

In some embodiments, the IDEs comprise one or more materials such as, for example, gold, platinum, and glassy carbon. In an exemplary embodiment, the IDEs comprise gold.

In some embodiments, the device provided herein further comprises a counter electrode and a reference electrode. In preferred embodiments, the IDE-based sensing device can be integrated with microelectronics for point-of-care (POC) applications to detect target diseases (e.g., HIV infection), manage treatments, and promote personalized healthcare regimes. In an exemplary embodiment, the sensing device can be integrated with one or more nanoelectromechanical systems (NEMS), microelectromechanical systems (MEMS), and miniaturized potentiostats.

The term "MEMS" herein broadly refers to small, mechanical devices constructed using techniques traditionally associated with integrated circuit wafer processing. Conventionally, MEMS devices generally range in size from 20 µm to 1 mm and comprise much smaller components ranging between 1 µm and 100 µm in size. A typical MEMS device comprises a central unit that processes data (i.e., the microprocessor) and several components that interact with the surroundings such as a sensing component. Exemplary MEMS devices include, but are not limited to, miniaturized gears, levers, cantilevers, and springs. Similarly, NEMS are electromechanical devices having dimensions on the order of nanometers and can be integrated with transistor-like electronics, moving parts (e.g., actuators and motors), and sensors. The low mass and high surface-to-volume ratio, among other properties, render NEMS advantageous for a variety of applications. The specific NEMS or MEMS devices that can be employed for the electrochemical sensing devices provided herein can vary in accordance with the target POC applications.

A potentiostat is an electronic hardware required to control a three-electrode (i.e., working electrode, counter electrode, and reference electrode) electrochemical cell and carry out electroanalytical experiments. In some embodiments provided herein, the potentiostat measures the current flow between the working electrode and counter electrode by controlling the voltage difference between the working electrode and the reference electrode. Any known potentiostat suitable for integration with a three-electrode cell comprising IDEs, NEMS, and/or MEMS devices can be adapted for use in the present invention, and those skilled in the art would recognize that the configuration of the potentiostat can be varied according to the target POC applications.

POC testing is particularly desirable for today's healthcare needs because it rapidly delivers results to medical practitioners and enables faster consultation. Early diagnosis allows a practitioner to begin treatment sooner and thus to avoid unattended deterioration of a patient's condition. Examples of existing POC analyses include, but are not limited to, tests for viral diseases, glucose, drugs of abuse, serum cholesterol, pregnancy, and ovulation. Advantageously, exemplary embodiments involving highly effective electrochemical sensing devices integrated with NEMS, MEMS, and/or miniaturized potentiostats can enable POC testing of the progression of viral diseases such as, for example, nuroAIDS, caused by HIV, without requiring elaborate laboratory testing equipment and apparatus.

In some embodiments, the electrochemical sensing device provided herein can monitor changes in the electrophysiology of cells such as, for example, human astrocytes, that have been infected with HIV and subsequently exposed to, and/or treated with, at least one of the following: a substance of abuse, an antagonist to the substance of abuse, and an HIV therapeutic drug (e.g., tenofevir)

The term "substance of abuse" refers to a substance that is psychoactive and that induces tolerance and/or addiction. Substances of abuse include, but are not limited to, stimulants (e.g., cocaine and amphetamines), opiates (e.g., morphine and heroin), cannabinoids (e.g., marijuana and hashish), nicotine, alcohol, substances that mediate agonist activity at the dopamine D2 receptor, and derivatives thereof. Substances of abuse include, but are not limited to recreational drugs and addictive medications. In an exemplary embodiment, the substance of abuse is cocaine (Coc).

Examples of recreational drugs include alcohol (ethyl alcohol); gamma hydroxybutyrate (GHB); caffeine; nicotine; *cannabis* (marijuana) and *cannabis* derivatives; opiates and other morphine-like opioid agonists such as heroin, phencyclidine and phencyclidine-like compounds; sedative such as benzodiazepines, methaqualone, mecloqualone, etaqualone, and barbiturates; and psychoactive stimulants (also known as psychostimulants) such as cocaine, amphetamines and amphetamine-related drugs such as dextroamphetamine, methamphetamine, and methylamphetamine. Other examples include, for example, hallucinogens such as LSD, psilocybin, and ecstasy. Examples of addictive medications include, for example, benzodiazepines; barbiturates; and pain medications such as alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, (e.g., OxyContin™), oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, mixed μ-agonists/antagonists, and the like.

Since drug antagonists are often administered to patients exposed to substances of abuse while receiving HIV treatments, some embodiments of the subject invention provide sensing devices capable of monitoring the combined effects of a substance of abuse, its antagonist, and/or an anti-HIV therapeutic agent.

Antagonists often act upon receptors, typically in the brain (and which may also be present in one or more other organs such as liver, lungs, and kidney) and competitively bind the receptor with higher affinity than the agonist, i.e., the substance of abuse, effectively blocking the receptor so as to prevent the body from responding to the substance of abuse, or in the case of compulsive behavior, more generally by blocking the positive reinforcing effect of the behavior. As explained herein, some antagonists useful in the subject invention may also produce a weak or partial agonist response. Partial agonists bind and activate a given receptor, but have only partial efficacy at the receptor relative to a full agonist. They may also be considered ligands that display both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. In preferred embodiments, rimcazole antagonist (RA) is used as an antagonist to Coc. The RA is a sigma ($\sigma 1$ & $\sigma 2$) receptor antagonist and dopamine reuptake inhibitor, having proven its potential in blocking the locomotor stimulant effects of Coc (Katz et al. 2003; Matsumoto et al. 2001).

The terms "therapeutic agent" and "drug," as used interchangeably herein, include any natural or synthetic substance that has a physiological effect when administered to an animal. As used herein, the terms "drug" and "therapeutic agent" include both therapeutic and diagnostic agents. The drug can be suitably employed in accordance with the invention with animals (i.e., subjects), particularly mammals including humans, veterinarian animals and farm animals. Drugs used in accordance with the subject invention can include those affecting, acting on, or being visualized at a desired target within, or on, the animal body, such as, for example, within the nervous system, including tumor tissue located therein.

In preferred embodiments, therapeutic agents provided herein are antiretroviral or viral latency-breaking drugs capable of treating and/or diagnosing one or more CNS diseases including, but not limited to, neuro-AIDS, brain tumors, other forms of cancer, Alzheimer's disease, Parkinson's disease, Huntington's disease, traumatic brain injury (TBI) and other neurodegenerative disorders. In preferred embodiments, the CNS disease is neuro-AIDS caused by HIV-1 infection, latent or otherwise.

As disclosed herein, neuro-AIDS can be, for example, any of the AIDS-related disorders of the CNS caused by the HIV virus, by certain cancers, by infections caused by bacteria, fungi, viruses, and the like, or by toxic effects of drugs used to treat such conditions. Non-limiting examples of neuro-AIDS include HIV-associated dementia (HAD), HIV-associated neurocognitive disorder (HAND), CNS lymphomas, Cryptococcal meningitis, and various psychological and neuropsychiatric disorders related to AIDS in the CNS.

In some embodiments, the drug is an antiretroviral drug selected from, for example, nucleoside reverse transcriptase inhibitors (NRTIs), non-nucleoside reverse transcriptase inhibitors (NNRTIs), nucleotide analog reverse transcriptase inhibitors (NtARTIs or NtRTIs), protease inhibitors (PIs), and integrase strand transfer inhibitors (INSTIs). In preferred embodiments, the antiretroviral drug is an NRTI such as, for example, tenofovir (Tef), which is a nucleotide analog preferred as a first-line NRTI and recommended for HIV eradication since 2001. Advantageously, tenofovir shows high efficacy at lower dose (i.e., administered once daily) and lower rate of treatment-limiting toxicity compared to other antiretroviral drugs, is well-tolerated by patients, is effective in treating cases of HIV-hepatitis B coinfection, is lower at cost, and does not cause anemia (Karim et al. 2010).

In some embodiments, the drug is a viral latency-activity drug selected from, for example, protein kinase C (PKC) agonists, histone deacetylase (HDAC) inhibitors, and nuclear factor kappa-light-chain-enhancer of activated B cells (NF-κB).

In some embodiments, one or more of the substances of abuse, their antagonises and the therapeutic agents can be chemically modified to include a chemical tagging agent. Examples include, but are not limited to, targeting antibodies, and targeting ligands, aptamers, and antigens, such as cancer antigens.

In another aspect, the subject invention provides methods of monitoring changes in the electrophysiological nature of cells utilizing the sensing devices provided herein as well as analytical technique such as, for example, electrochemical impedance spectroscopy (EIS).

In some embodiments, the three-electrode sensing device comprising IDEs as provided herein is integrated with a cell cultureware in which cells in a biological sample can be stored and measured subsequently using EIS. In some embodiments, the cell cultureware also comprises a redox probing moiety dissolved in a physiologically acceptable fluid.

The sensitivity of an electrochemical sensing device is influenced by the selected electrochemical transduction method by which the sensing signals are detected and subsequently processed. Some embodiments provide that electrical potential, frequency, or current can be applied to the sensing device in order to produce electrochemical responses in the cells being examined. In exemplary embodiments, biologically suitable transduction methods for detecting electrophysiological changes of CNS and/or PNS nerve cells (e.g., HA cells) include, for example, electrochemical impedance spectroscopy (EIS, whose output is in terms of impedance or resistance) and cyclic voltammetry (CV, whose output is in terms of current). In certain embodiments of the subject invention, both CV and EIS can be used to detect the electrophysiological changes of the cells using the electrochemical sensing device provided herein. In preferred embodiments, EIS is used to detect the electrophysiology of infected and/or therapeutically treated nerve cells.

Other analytical methods are also available for measuring the electrochemical response of the device. Non-limiting examples include chronoamperometry, chronovoltammetry, and differential pulse voltammetry. Persons of ordinary skill in the art would recognize that other suitable electrochemical techniques, now known or hereafter developed, can also be employed to detect a target antigen using the electrochemical sensing devices provided herein.

Advantageously, the method of detecting progression of HIV infection provided herein is rapid and can be completed in about 10 minutes to about 20 minutes. In some embodiments, the method can be completed in about 11 minutes, about 13 minutes, about 15 minutes, about 17 minutes, or about 19 minutes. In some embodiments, the method can be completed in about 12.5 minutes, about 16.5 minutes, or about 19.5 minutes.

In an exemplary embodiment, the subject invention provides a method of monitoring the electrophysiology of HIV-infected human astrocytes (HA) after being exposed to cocaine with or without subsequent treatment involving antagonists (e.g., RA) and antiretroviral drugs (e.g., Tef) (FIG. 1B). HA is a preferred model cell type in the present invention because Coc has been known to affect the electrophysiology of HA in a rapid manner (FIG. 1A). Specifically, when subjected to treatment by Coc and/or therapeutic agents, HA cells attempt to regain their natural condition by secreting various inflammatory agents that alter the intra- and extracellular environment, leading to changes in the electrophysiological nature of the cells. Electrophysiological changes described herein can be monitored by measuring the electrochemical impedance of the cells expressed in terms of their charge transfer resistance ($R_{ct}$).

In some embodiments, the biological sample comprising CNS and/or PNS cells can be, for example, human physiological fluids, cell cultures, tissues, and environmental samples. In specific embodiments, the sample is a human physiological fluid selected from blood, plasma, semen, serum, saliva, urine, and tears.

Any suitable method for contacting the electrochemical sensing substrate with the sample may be used. For example, suitable methods include rinsing, dipping, or immersing the sensing substrate in a sample, passing a stream comprising the sample over the substrate, or a combination thereof. Any known method of contacting a substrate with a sample can be adapted for use in the present invention, and those skilled in the art would recognize that the duration of immersion can be varied within a reasonable range.

Advantageously, the electrochemical sensing methods provided herein can enable rapid, sensitive, and selective monitoring of HIV-infection and subsequent therapeutic treatments in CNS cells of patients exposed to substances of abuse. Electrophysiological information collected using integrated sensing devices and methods provided herein is useful for timely HIV disease management in various in-field, on-site diagnostic POC applications.

Other objects, features, and advantages of the invention will be apparent to those skilled in the art from the detailed description of the invention which will now follow, taken in conjunction with the tables, drawings, and the accompanying claims.

EXAMPLES

The following are examples that illustrate the aforementioned embodiments and should not be construed as limiting.

All data are presented as the mean±the standard deviation of the mean (S.D). The results were analyzed using ANOVA (Kruskal-Wallis test) followed by Dunn's Multiple Comparison post-test to determine statistical significance (Graph Pad 5 Software, Inc., La Jolla, Calif., USA). Significance was considered to be $p<0.05$.

Example 1

A cultureware chip (CC) comprising eight wells was procured from Applied Biophysics (#8WCP PET arrays) and used to grow HA for HIV infection and subsequent drug treatments. Each well (substrate area of 0.8 $cm^2$ and maximum volume of 600 μL) of the CC comprised a sensing substrate configured to have gold-based IDE (IDE-Au; surface area: 3.985 $mm^2$). In each well and on the sensing substrate, the IDE-Au array was useful to grow a large number of cells (e.g., approximately between 4000 and 8000) and designed in such a way to perform electrochemical measurements without fluctuation.

EIS was conducted in 400 μL of 5 mM PBS (pH 7.4) comprising 5 mM Fe (II)/Fe(III) as redox moieties using VMP3, a multi-channel potentiostat/galvanostats obtained from BioLogic Instruments. Each EIS measurement was made in sets of triplet and an average was used for analytical interpretation. Before processing the CC for cell culture, EIS measurement was made on cells of each well. The results of the EIS study confirmed that each well of CC exhibited repeatable and reproducible electrochemical response within 2 to 3% of variation. The cyclic voltammetry (CV) studies were also performed on CC using identical experimental conditions to validate results obtained using EIS.

Figure 2A:
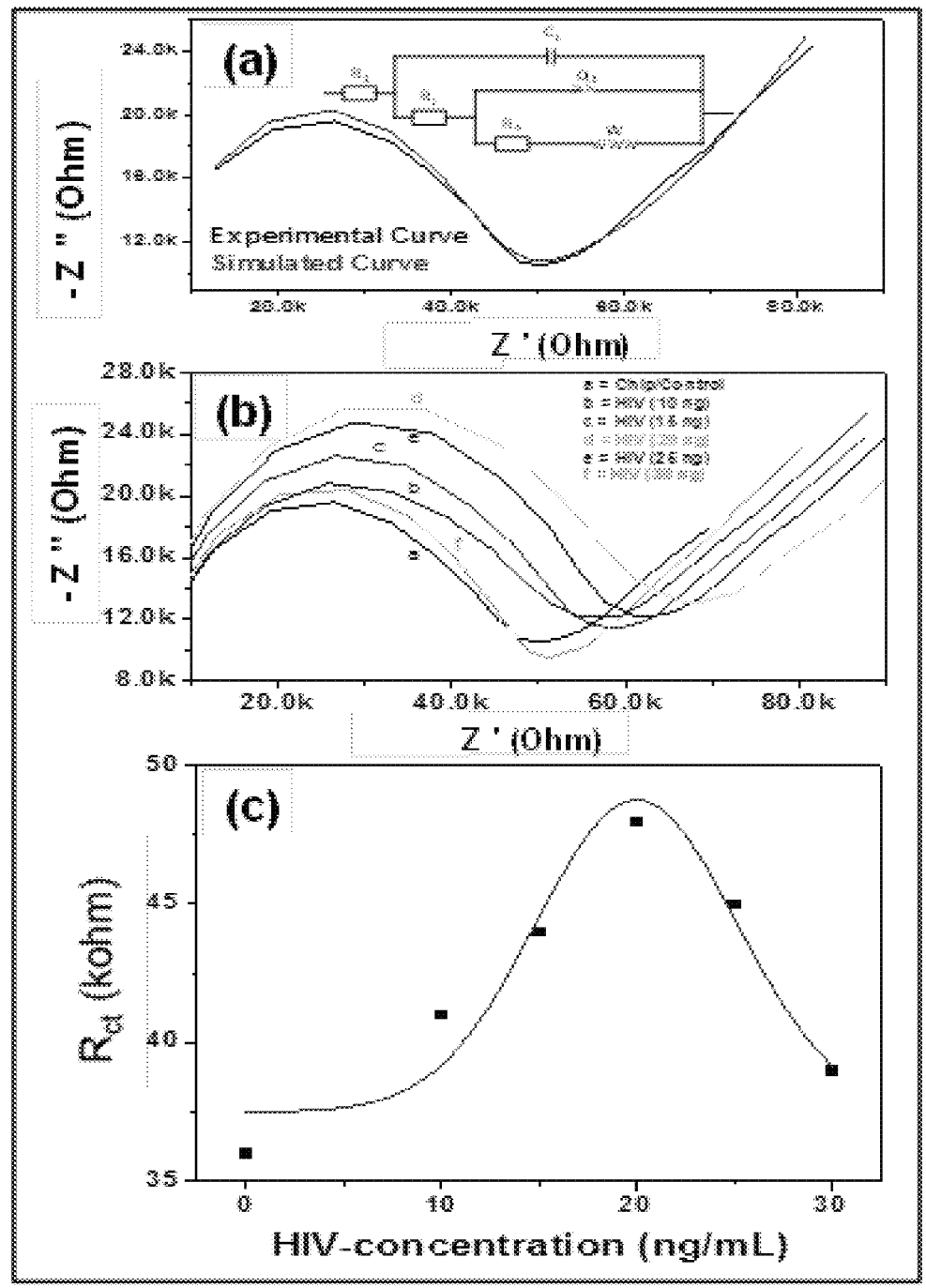
FIG. 2A shows a set of EIS measurements of HA cells grown in the well of a cultureware, where results in (a) were obtained using 400 μL of 5 mM PBS (pH 7.4) comprising 5 mM Fe (II)/Fe(III) as redox moieties. Experimentally obtained data was simulated using an electronic circuit (inset in FIG. 2A (a)). In (b), the EIS measurements were acquired as a function of the concentration of HIV. In (c), variations in charge transfer resistance ($R_{ct}$) of the cells as a function of HIV concentration is depicted.

The EIS of cells grown on IDE-Au exhibited a Nyquist plot (black curve in FIG. 2 A (a)), in which the experimentally obtained data matched well with the simulated results (red curve in FIG. 2A (a)) using an electronic circuit (inset of FIG. 2A (a)). A portion of the Nyquist plot of cells grown on IDE-Au takes on a semicircle shape at higher frequency that corresponds to the electron-transfer limited process. The radius of this semicircle represents the charge transfer resistance, $R_{ct}$, of the system. The semicircle is followed by a linear portion of the curve (45° to the axes) corresponding to the diffusion-controlled electron transfer process (Kaushik et al. 2010).

For a biological system, the $R_{ct}$ value varies little in intra/extracellular cell properties, such as the electrical and physical properties of the HA. As a result, $R_{ct}$ was selected as the parameter for the assessment of HIV infection in HA and on treatments with Coc and drugs specific to both HIV and Coc. The EIS was performed on HA as a function of HIV infection doses which varies from 10 ng/mL to 30 ng/mL (FIG. 2A (b)).

Example 2

Primary HA were purchased from ScienCell Research Laboratories (Carlsbad, Calif.; Cat. #1800-5) and grown in astrocyte medium purchased from ScienCell Laboratories (Cat. #1801) comprising 2% of fetal bovine serum (ScienCell Cat. #0010), astrocyte growth supplement (ScienCell Cat. #1852), and penicillin/streptomycin (ScienCell Cat. #0503). HIV-1$_{Ba-L}$ (clade B) (NIH AIDS Reagent Program Cat. #510) was obtained through AIDS Research and Reference Reagent Program, Division of AIDS, NIAID, NIH. The Cocaine hydrochloride-Sigma (Cat# C5776), rimcazole dihydrochloride-Tocris (1497, CAS#75859-03-9), and tenofovir disoproxil fumarate-Sigma (1643656; CAS #202138-50-9) were also obtained for this research.

Primary HA were grown in the eight-well CC plate at a concentration of approximately 8,000 cells and infected with different concentrations (ranging from 10 ng/mL to 30 ng/mL) of HIV-1 using a previously described protocol (Atluri et al. 2013; Eugenin and Berman 2007). Each well was used for a separate treatment.

After overnight infection, unabsorbed virus was washed away using PBS (pH 7.4), and the infected cells were cultured for 5 days in the presence or absence of Coc (1 µM). RA (2 µM) was added to the designated wells (specific to Coc) 2 h before each treatment involving Coc. The optimized dose of Coc selected for this study was 1 µM, which was based on our dose response study for cytotoxicity and HIV infectivity (Roy et al. 2015).

On the 5$^{th}$ day, 100 µg (100 µL of 1 mg/mL) of Tef was added to wells specific to HIV and incubated for 7 days in total. The dose of Tef was selected on the basis of its toxicity and efficacy as reported in our previous publication (Jayant et al. 2015).

On every second day, fresh medium was added and after 7 days of HIV infection, culture supernatants were collected for the p24 antigen estimation using an ELISA kit (ZeptoMetrix Corp. Cat #0801200).

In comparison to HA grown onto IDE-Au, the $R_{ct}$ and the Warburg impedance parameters of the CC were found responsive to additions of HIV doses. The results showed that the value of $R_{ct}$ first increased from 36 to 48 KΩ when treated with different doses of HIV ranging from 10 ng/mL to 20 ng/mL and then decreased when the infection level continued to increase to between about 25 ng/mL to 30 ng/mL (FIG. 2 A (c)). The increase in $R_{ct}$ value at the early stage of infection might be due to the presence of virus in cellular environment that later attached to mannose receptors (Barre-Sinoussi et al. 2013). However, $R_{ct}$ decreased from 44 to 39 KΩ when HIV doses increased to more than 20 ng/mL. This may be due to internalization or fusion of virus genome into the cell, where virus genome multiplies by reverse transcription and replicates DNA that integrates with genome of HA and also induces the production of various cytokines, chemokines, neurotoxic factor, and extracellular toxic viral proteins (Barre-Sinoussi et al. 2013). These alterations in cell physiology ultimately make the cell weak and electroactive.

Example 3

450 µl of undiluted HA culture supernatant was mixed with 50 µL of lysing buffer. 200 µL of this lysed sample along with standards were added in duplicates into each microtiter plate well coated with HIV-1 p24 antibody and incubated overnight at 37° C. Samples were aspirated and each plate was washed 6 times. 100 µL of reconstituted HIV-1 p24 detector antibody was added to each well and incubated for 1 h at 37° C. After washing the plate, 100 µL of the Streptavidin-Peroxidase Working Solution was added to each well and incubated for 30 min at 37° C. Again after washing, 100 µL of Substrate Working Solution was added to all wells and incubated uncovered for 30 minutes at room temperature. After incubation, 100 µL of stop solution was added to each well and the optical density of each well was read at 450 nm using a microplate reader (Yndart et al. 2015). This study will be of use to assess the production and variation of p24 antigen due to HIV infection and other treatments.

Example 4

The MTT cell viability assay was examined using a modified assay method as described by Rao et al (Kurapati et al. 2012). After 7 days of HIV-infection and/or treatment with an optimum concentration of Coc (1 µM), 6-well plates were given media change with 1 mL of medium. Then, 100 µL of MTT (100 mg MTT/20 ml PBS) was added to each well and the wells were incubated for 3 h at 37° C. Further, one volume of stop mix solution was added to each well. The plates were then rocked for about 2 h and centrifuged.

The optical density of the solubilized formazan was determined spectrophotometrically measuring the absorbance at 550 nm after transferring into the 96-well plate. The optical density of formazan in each well is directly proportional to the cell viability and utilized for calculations.

Considering cell viability as a major factor, HA toxicity was evaluated in terms of cell viability as a function of levels of HIV infection ranging from 10 ng/mL to 30 ng/mL using MTT assay.

The results of this study confirmed that 90 to 95% of the HA cells were viable at HIV doses ranging from 10 ng/mL to 20 ng/mL. However, HA cells with HIV dose of more than 20 ng/mL resulted in cell viability of less than 80%. Thus, an HIV-infection level of 20 ng/mL was used for further experiments.

Figure 2B:
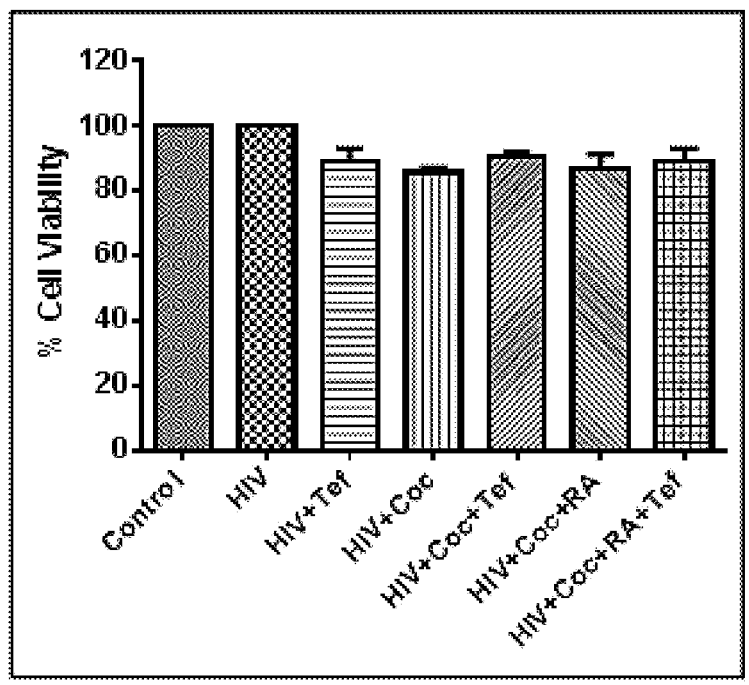
FIG. 2B shows the evaluation of the viability of HA cells following treatments with cocaine and drugs using MTT-assay.

The cell viability of HA infected with HIV, treated with Coc followed by treatment using Tef and RA is shown in FIG. 2B. The HIV infection and subsequent treatments showed cell viability in the range of 90 to 96%, confirming that each treatment is not affecting health of the cells. However, the cell viability on HA treated with Coc was lower (~85%) due to rapid impairment of HA by Coc, in comparison to other neuronal cells.

Example 5

Figure 2C:
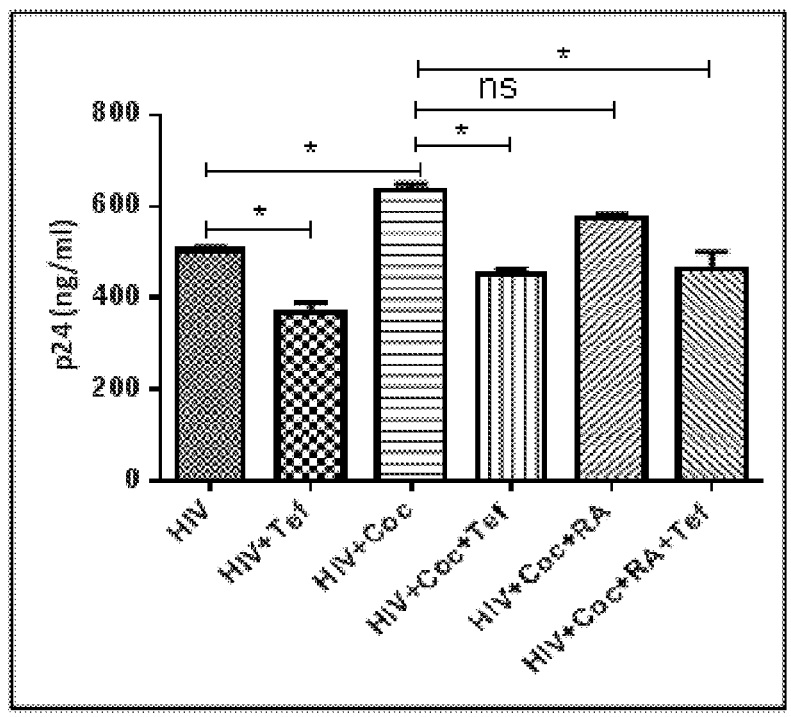
FIG. 2C shows the estimation of p24 variation in HA cells following infection with HIV and treatments with cocaine and drugs.

The assessment of the level of HIV infection in HA following exposure to Coc and other drugs (e.g., RA and/or Tef) was also evaluated by estimating the p24 antigen levels using ELISA techniques (FIG. 2 C). A significant increase in HIV dose was observed in the presence of Coc (p<0.006) when compared to only HIV-infected cells (FIG. 2C). This is because it is a well-known fact that consumption of Coc facilitates progression of HIV infection (Dahal et al. 2015).

Following the treatment with Tef, a significant reduction in the level of HIV infection was observed in comparison to HIV-infected cells alone, confirming the therapeutic effects of Tef.

Considering the synergistic effects of anti-HIV drug and Coc antagonist, HA infected with HIV and Coc were treated with Tef and RA together. A significant reduction of HIV-infection level was observed, which reveals that both RA and Tef can be used together to control HIV infection and block the effects induced by Coc. Although a reduction in infection levels in the presence of Coc and RA compared to cells treated with HIV and Coc alone has been observed, it is not statistically significant.

Example 6

To evaluate variations in HIV infection as a function of the $R_{ct}$ value (FIGS. 3A-3D) measured using EIS, an experiment was planned in 9 wells as described in FIGS. 3A-3D.

Figure 3A:
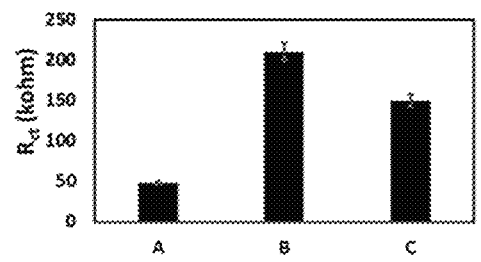
FIGS. 3A-3D show the results of EIS measurements acquired in a cultureware integrated with an exemplary electrochemical sensing substrate. The cells in each well of the cultureware were treated, respectively, with HA, HIV, Coc, Tef, RA, and various combinations of the above. Combinations A-I represent the treatment of the cells in each of the 9 wells in the cultureware (as designated in the figures). $1^{st}$ well A=HA, $2^{nd}$ well B=HA+HIV, $3^{rd}$ well C=HA+HIV+Tef, $4^{th}$ well D=HA+Coc, $5^{th}$ well E=HA+Coc+RA, $6^{th}$ well F=HA+HIV+Coc, $7^{th}$ well G=HA+HIV+Coc+RA, $8^{th}$ well H=HA+HIV+Coc+Tef, $9^{th}$ well I=HA+HIV+Coc+Tef+RA.

It was observed that the value of $R_{ct}$ of HA increased from 48 to 210 KS on HIV infected-HA (20 ng/mL) (FIG. 3A). This suggests that the presence of virus in the cellular environment hindered the electron transport from mediator to the sensing substrate IDE-Au. After treating HIV-infected HA with Tef, the value of $R_{ct}$ decreased from 210 to 150 KΩ, confirming that the anti-HIV drug Tef eradicated the virus in the cellular environment, thus inducing HA to behave normally. This also confirmed the sensitivity of the sensing substrate for understanding the drug resistance towards viral progression.

The treatment of Coc on HA decreased the $R_{ct}$ value significantly to 21 KS in comparison to normal HA. This might be due to the rapid effect of Coc on the chemical and biological activities of HA. The Coc is known to cause HA toxicity via rapid impairment. Besides, Coc also facilitates the secretion of various electro-active inflammatory agents resulting in easier electron transfer from medium to IDE-Au. These secreted agents alter the chemical, physical, and biological features of HA, making the cells electrically conductive. This phenomenon could facilitate the transfer of electrons from the medium to the sensing substrate IDE-Au resulting in a lower $R_{ct}$ value than what uninfected, untreated HA would have.

Figure 3B:
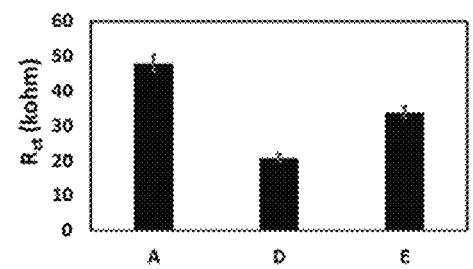

As expected, when treating Coc-treated HA with RA, the value of $R_{ct}$ increased to 34 KΩ (FIG. 3B). This suggests that the therapeutic action of RA is to block the effects induced by Coc impairment in HA.

Example 7

Figure 3C:
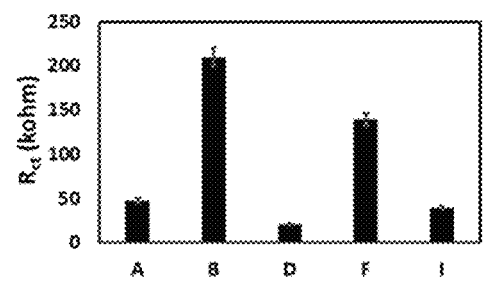

The effect of Coc on the level of HIV infection in HA cells was explored (FIG. 3C). The value of $R_{ct}$ of HIV-infected HA treated with Coc was found to be higher (140 KS) than HA+Coc and HA+Coc+RA (34 KΩ). This confirmed that Coc facilitated HIV infection in HA cells. This excess of virus in the cellular media hinders electron transport to the sensing substrate IDE-Au and thus increased the value of $R_{ct}$.

Figure 3D:
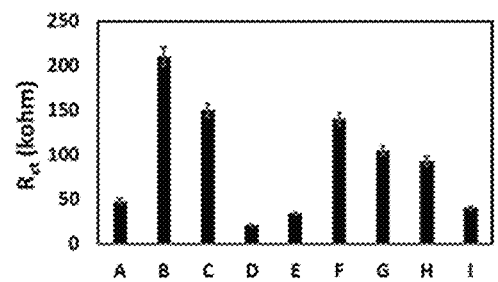
Figure 4A:
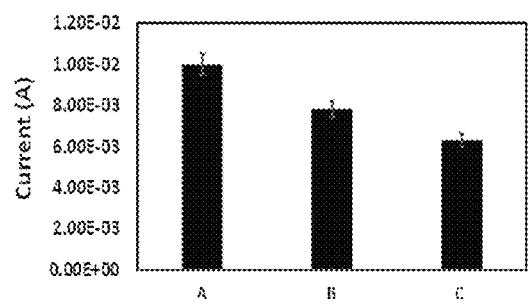
FIGS. 4A-4D show results of CV measurements acquired in a cultureware integrated with an exemplary electrochemical sensing substrate. The cells in each well of the cultureware were treated, respectively, HA, HIV, Coc, Tef, RA, and various combinations of the above. $1^{st}$ well A=HA, $2^{nd}$ well B=HA+HIV, $3^{rd}$ well C=HA+HIV+Tef, $4^{th}$ well D=HA+Coc, $5^{th}$ well E=HA+Coc+RA, $6^{th}$ well F=HA+HIV+Coc, $7^{th}$ well G=HA+HIV+Coc+RA, $8^{th}$ well H=HA+HIV+Coc+Tef, $9^{th}$ well I=HA+HIV+Coc+Tef+RA.
Figure 4B:
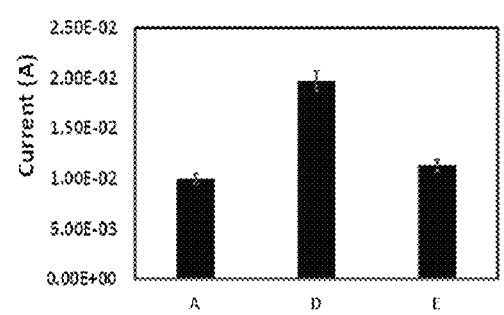
Figure 4C:
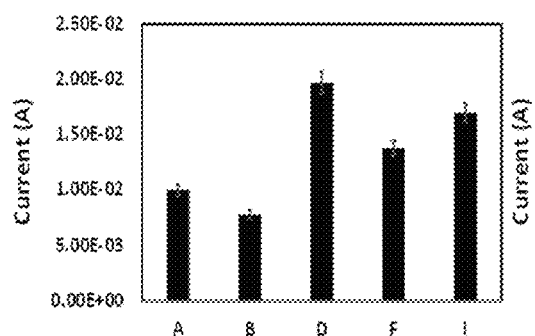
Figure 4D:
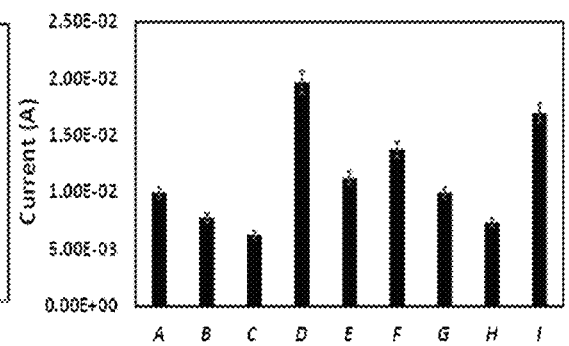

To explore the synergistic effects of Tef and RA, an EIS study was performed on HA treated with HIV and Coc together (FIG. 3D). The $R_{ct}$ value of HA infected with HIV in the presence of Coc decreased to 105 KΩ when treated with RA, suggesting that RA again blocked the effects caused by Coc. The further decrease in $R_{ct}$ of HA+HIV-infection+Coc to 93 KS following the treatment with Tef confirmed the therapeutic actions of the drug. Moreover, HA treated with HIV and Coc together following the treatment with Tef and RA also decreased $R_{ct}$ to 40 KΩ, again confirming the therapeutic action of both drugs. During this phenomenon, Tef and RA both participated in therapeutic actions with Tef eradicating the HIV infection and RA eliminating the impairment caused by Coc consumption.

The therapeutic action of the drugs makes infected cells behave as normal HA. This affected the charge transfer of electrons generated by Fe (II)/Fe (III) conversion and can be monitored via analysis of variations in the value of $R_{ct}$.

Together, these results suggest that FDA-approved drugs (e.g., Tef) and antagonist drugs (e.g., Ar) may work together to eradicate HIV infection and to block the adverse effects induced by Coc in a cell line.

Example 8

The results of the EIS study (FIGS. 3A-3D) were found similar to those as obtained using CV techniques in assessing HIV infection with respect to HIV infections and subsequent treatments (FIGS. 4A-4D). In the CV study, the assessment of HIV infection in HA following the treatment of Coc, Tef, and RA was detected as a function of current. The results of the CV studies are in agreement with the EIS outcomes.

The selection of a transduction method is crucial to developing a miniaturized real-time monitoring system. This is the reason why the same study was conducted using two electrochemical methods. Based on the biological system and the system design requirement, either EIS or CV can be selected. However, drug-drug interactions and the side effects of progression of HIV infection following the use of substance of abuse (e.g., Coc) cannot be underestimated during disease monitoring.

The examples and embodiments described herein are for illustrative purposes only and various modifications or changes in light thereof will be apparent to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Atluri, V., Kanthikeel, S. P., Reddy, P., Yndart, A., Nair, M., 2013. Human synaptic plasticity gene expression profile and dendritic spine density changes in HIV-infected human CNS cells: role in HIV-associated neurocognitive disorders (HAND). PLoS One 8(4), e61399.

Barre-Sinoussi, F., Ross, A. L., Delfraissy, J.-F., 2013. Past, present and future: 30 years of HIV research. Nat Rev Micro 11(12), 877-883.

Cheng, X., Liu, Y.-s., Irimia, D., Demirci, U., Yang, L., Zamir, L., Rodriguez, W. R., Toner, M., Bashir, R., 2007. Cell detection and counting through cell lysate impedance spectroscopy in microfluidic devices. Lab on a Chip 7(6), 746-755.

Cohen, A. E. and Kunz, R. R, 2000. Sensors and Actuators B: Chemical, 62, 23.

Cruz, A. F. D., Norena, N., Kaushik, A., Bhansali, S., 2014. A low-cost miniaturized potentiostat for point-of-care diagnosis. Biosensors and Bioelectronics 62, 249-254.

Dahal, S., Chitti, S. V., Nair, M. P., Saxena, S. K., 2015. Interactive effects of cocaine on HIV infection: implication in HIV-associated neurocognitive disorder and neuroAIDS. Frontiers in microbiology 6, 931.

Eugenin, E. A., Berman, J. W., 2007. Gap junctions mediate human immunodeficiency virus-bystander killing in astrocytes. The Journal of Neuroscience 27(47), 12844-12850.

Iwasaki, Y. and Morita, M., 1995. Current Separations, 14, 1.

Jayant, R., Atluri, V., Agudelo, M., Sagar, V., Kaushik, A., Nair, M, 2015. Sustained-release nanoART formulation for the treatment of neuroAIDS. International Journal of Nanomedicine 10, 1077-1093.

Karim, Q. A., Karim, S. S. A., Frohlich, J. A., Grobler, A. C., Baxter, C., Mansoor, L. E., Kharsany, A. B., Sibeko, S., Mlisana, K. P., Omar, Z., 2010. Effectiveness and safety of tenofovir gel, an antiretroviral microbicide, for the prevention of HIV infection in women. science 329 (5996), 1168-1174.

Katz, J. L., Libby, T. A., Kopajtic, T., Husbands, S. M., Newman, A. H., 2003. Behavioral effects of rimcazole analogues alone and in combination with cocaine. European Journal of Pharmacology 468(2), 109-119.

Kaushik, A., Jayant, R. D., Nikkhah-Moshaie, R., Bhardwaj, V., Roy, U., Huang, Z., Ruiz, A., Yndart, A., Atluri, V., El-Hage, N., Khalili, K., Nair, M., 2016a. Magnetically guided central nervous system delivery and toxicity evaluation of magneto-electric nanocarriers. Scientific Reports 6, 25309.

Kaushik, A., Jayant, R. D., Sagar, V., Nair, M., 2014a. The potential of magneto-electric nanocarriers for drug delivery. Expert opinion on drug delivery 11(10), 1635-1646.

Kaushik, A., Jayant, R. D., Tiwari, S., Vashist, A., Nair, M., 2016b. Nano-biosensors to detect beta-amyloid for Alzheimer's disease management. Biosensors and Bioelectronics 80, 273-287.

Kaushik, A., Solanki, P. R., Kaneto, K., Kim, C., Ahmad, S., Malhotra, B. D., 2010. Nanostructured iron oxide platform for impedimetric cholesterol detection. Electroanalysis 22(10), 1045-1055.

Kaushik, A., Tiwari, S., Jayant, R. D., Marty, A., Nair, M., 2016c. Towards detection and diagnosis of Ebola virus disease at point-of-care. Biosensors and Bioelectronics 75, 254-272.

Kaushik, A., Vasudev, A., Arya, S. K., Pasha, S. K., Bhansali, S., 2014b. Recent advances in cortisol sensing technologies for point-of-care application. Biosensors and Bioelectronics 53, 499-512.

Kaushik, A., Yndart, A., Jayant, R. D., Sagar, V., Atluri, V., Bhansali, S., Nair, M., 2015. Electrochemical sensing method for point-of-care cortisol detection in human immunodeficiency virus-infected patients. International Journal of Nanomedicine 10(10), 677-685.

Kurapati, K. R. V., Samikkannu, T., Kadiyala, D. B., Zainulabedin, S. M., Gandhi, N., Sathaye, S. S., Indap, M. A., Boukli, N., Rodriguez, J. W., Nair, M. P., 2012. Combinatorial cytotoxic effects of *Curcuma longa* and *Zingiber officinale* on the PC-3M prostate cancer cell line. Journal of basic and clinical physiology and pharmacology 23(4), 139-146.

Luongo, K., Holton, A., Kaushik, A., Spence, P., Ng, B., Deschenes, R., Sundaram, S., Bhansali, S., 2013. Microfluidic device for trapping and monitoring three dimensional multicell spheroids using electrical impedance spectroscopy. Biomicrofluidics 7(3), 034108.

Mahmoud, K. A., Luong, J. H., 2008. Impedance Method for Detecting HIV-1 Protease and Screening For Its Inhibitors Using Ferrocene—Peptide Conjugate/Au Nanoparticle/Single-Walled Carbon Nanotube Modified Electrode. Analytical chemistry 80(18), 7056-7062.

Matsumoto, R. R., Hewett, K. L., Pouw, B., Bowen, W. D., Husbands, S. M., Cao, J. J., Hauck Newman, A., 2001. Rimcazole analogs attenuate the convulsive effects of cocaine: correlation with binding to sigma receptors rather than dopamine transporters. Neuropharmacology 41(7), 878-886.

Nair, M., Jayant, R. D., Kaushik, A., Sagar, V., Getting into the brain: Potential of nanotechnology in the management of NeuroAIDS. Advanced Drug Delivery Reviews.

Roy, U., Atluri, V. S., Agudelo, M., Yndart, A., Huang, Z., Nair, M., 2015. DJ1 expression downregulates in neuroblastoma cells (SK-N-MC) chronically exposed to HIV-1 and cocaine. Frontiers in microbiology 6.

Ruiz, A., Nair, M., Kaushik, A., 2015. Recent update in NanoCure of NeuroAIDS. Science Letters Journal 4, 172.

Shafiee, H., Asghar, W., Inci, F., Yuksekkaya, M., Jahangir, M., Zhang, M. H., Durmus, N. G., Gurkan, U. A., Kuritzkes, D. R., Demirci, U., 2015a. Paper and flexible substrates as materials for biosensing platforms to detect multiple biotargets. Scientific reports 5.

Shafiee, H., Jahangir, M., Inci, F., Wang, S., Willenbrecht, R., Giguel, F. F., Tsibris, A., Kuritzkes, D. R., Demirci, U., 2013a. Acute On-Chip HIV Detection Through Label-Free Electrical Sensing of Viral Nano-Lysate. Small 9(15), 2553-2563.

Shafiee, H., Jahangir, M., Inci, F., Wang, S., Willingbrecht, R., Guigel, F., Kuritzkes, D., Demirci, U., 2013b. Acute HIV detection by viral lysate impedance spectroscopy on a microchip. Solid-State Sensors, Actuators and Microsystems (TRANSDUCERS & EUROSENSORS XXVII), 2013 Transducers & Eurosensors XXVII: The 17th International Conference on, pp. 2141-2144. IEEE.

Shafiee, H., Kanakasabapathy, M. K., Juillard, F., Keser, M., Sadasivam, M., Yuksekkaya, M., Hanhauser, E., Henrich, T. J., Kuritzkes, D. R., Kaye, K. M., 2015b. Printed Flexible Plastic Microchip for Viral Load Measurement through Quantitative Detection of Viruses in Plasma and Saliva. Scientific reports 5.

Shafiee, H., Lidstone, E. A., Jahangir, M., Inci, F., Hanhauser, E., Henrich, T. J., Kuritzkes, D. R., Cunningham, B. T., Demirci, U., 2014. Nanostructured optical photonic crystal biosensor for HIV viral load measurement. Scientific reports 4, 4116.

Shafiee, H., Wang, S., Inci, F., Toy, M., Henrich, T. J., Kuritzkes, D. R., Demirci, U., 2015c. Emerging technologies for point-of-care management of HIV infection. Annual review of medicine 66, 387-405.

Shah, P., Kaushik, A., Zhu, X., Zhang, C., Li, C.-Z., 2014. Chip based single cell analysis for nanotoxicity assessment. Analyst 139(9), 2088-2098.

Tokel, O., Yildiz, U. H., Inci, F., Durmus, N. G., Ekiz, O., Turker, B., Cetin, C., Rao, S., Sridhar, K., Natarajan, N., 2015. Portable Microfluidic Integrated Plasmonic Platform for Pathogen Detection. Scientific reports 5.

Vasudev, A., Kaushik, A., Tomizawa, Y., Norena, N., Bhansali, S., 2013. An LTCC-based microfluidic system for label-free, electrochemical detection of cortisol. Sensors and Actuators B: Chemical 182, 139-146.

Yager, P., Domingo, G. J., Gerdes, J., 2008. Point-of-care diagnostics for global health. Annu. Rev. Biomed. Eng. 10, 107-144.

Yang, Y., Yao, H., Lu, Y., Wang, C., Buch, S., 2010. Cocaine potentiates astrocyte toxicity mediated by human immunodeficiency virus (HIV-1) protein gp120. PLoS One 5(10), e13427.

Yndart, A., Kaushik, A., Agudelo, M., Raymond, A., Atluri, V. S., Saxena, S. K., Nair, M., 2015. Investigation of Neuropathogenesis in HIV-1 Clade B and C Infection Associated with IL-33 and ST2 Regulation. ACS chemical neuroscience 6(9), 1600-1612.

We claim:

1. A method for measuring changes in electrophysiology of cells, comprising:
    a) providing a device comprising a working electrode, a counter electrode, and a reference electrode, the working electrode being an electrochemical sensing substrate comprising an array of interdigitated electrodes;
    b) contacting the device with a biological sample comprising central nervous system (CNS) cells and/or peripheral nervous system (PNS) cells infected by human immunodeficiency virus (HIV), which are treated with at least one of the following agents: a substance of abuse, an antagonist of the substance of abuse, and a therapeutic agent, both the device and the biological sample being situated in a cell cultureware in which there is also an electrochemical redox moiety dissolved in a physiological fluid;
    c) subjecting the device to an applied potential, frequency, or current;
    d) monitoring the electrochemical response of the cells; and
    e) determining changes in the electrophysiology of the cells by comparing the measured electrochemical response of the cells with pre-determined control measurements.

2. The method according to claim 1, wherein the substance of abuse is cocaine.

3. The method according to claim 1, wherein the therapeutic agent is a nucleoside reverse transcriptase inhibitor (NRTI) based anti-HIV drug.

4. The method according to claim 3, wherein the therapeutic agent is tenofovir.

5. The method according to claim 1, wherein the device is further integrated with one or more components selected from microelectromechanical systems (MEMS), nanoelectromechanical systems (NEMS), and miniaturized potentiostats.

6. A method for measuring changes in electrophysiology of cells, comprising:
    a) providing a device comprising a working electrode, a counter electrode, and a reference electrode, the working electrode being an electrochemical sensing substrate configured to comprise an array of gold interdigitated electrodes;
    b) contacting the device with a biological sample comprising central nervous system (CNS) cells infected with human immunodeficiency virus (HIV), the cells having been treated with at least one of the following active agents: cocaine, an antagonist of cocaine, and tenofovir, both the device and the sample being situated in a cell cultureware in which there is also an electrochemical redox moiety dissolved in a physiological fluid;
    c) subjecting the device to an applied potential, frequency, or current;
    d) monitoring the electrochemical response of the cells; and
    e) determining changes in the electrophysiology of the cells by comparing the measured electrochemical response of the cells with pre-determined control measurements, the time required to measure changes in the electrophysiology of the cells being less than 20 minutes.

* * * * *